United States Patent [19]

Clapp-Shapiro et al.

[11] Patent Number: 5,801,172

[45] Date of Patent: Sep. 1, 1998

[54] **ANTIFUNGAL AGENT FROM *SPOROMIELLA MINIMOIDES***

[75] Inventors: Wendy H. Clapp-Shapiro, New York, N.Y.; Bruce W. Burgess, Passaic, N.J.; Robert A. Giacobbe, Lavallette, N.J.; Guy H. Harris, Cranford, N.J.; Suzanne Mandala, Scotch Plains, N.J.; Jon Polishook, Cranford, N.J.; Mark Rattray, Somerset, N.J.; Rosemary A. Thornton, Cranford, N.J.; Deborah L. Zink, Manalapan, N.J.; Angeles Cabello, Madrid, Spain; Maria Teresa Diez, Madrid, Spain; Isabel Martin, Madrid, Spain; Fernando Pelaez, Madrid, Spain

[73] Assignee: Merck & Co., Inc., Rahway, N.J.

[21] Appl. No.: 890,772

[22] Filed: Jul. 11, 1997

[51] Int. Cl.$^6$ .................. C07D 471/00; A01N 43/58
[52] U.S. Cl. ........................... 514/250; 544/346
[58] Field of Search ..................... 544/346; 514/250

[56] References Cited

PUBLICATIONS

Huang et. al., "New Fungal Metabolites . . .", Can. J. Bot., vol. 75 (Suppl. 1, Sect. E–H), 1995, pp. S898–S906.

*Primary Examiner*—Mukuho J. Shan
*Assistant Examiner*—Tamthom T. Ngo
*Attorney, Agent, or Firm*—Elliott Korsen; Mark R. Daniel

[57] ABSTRACT

There is disclosed a novel compound having the formula

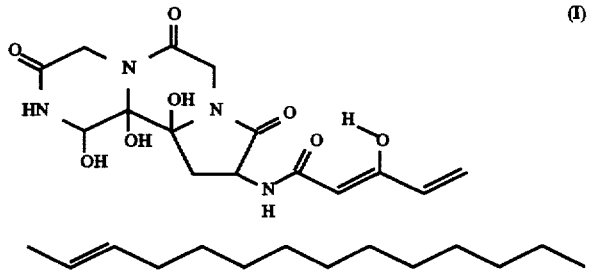

which exhibits antifungal activity.

8 Claims, No Drawings

ANTIFUNGAL AGENT FROM *SPOROMIELLA MINIMOIDES*

This is a continuation of a provisional application Ser. No. 60/021,454, filed Jul. 17, 1996.

BACKGROUND OF THE INVENTION

The present invention relates to a novel antifungal compound, compositions containing the compound and methods of using the compound. The compound and compositions exhibit broad spectrum antifungal activity against both human and plant fungal pathogens.

Clinical treatment of human fungal infections has relied mainly on two types of antifungal agents. These agents are amphotericin B, flucytosine and nystatin, which are fungicidal and capable of curing fungal infections at the cost of severe side effects to the patient, and fluconazole and other azole agents, which exhibit fewer side effects but are only fungistatic.

Current available crop protection agents may be susceptible to the development of resistance and limited in their spectrum of activity.

Thus, there is a need for new human and plant antifungal agents.

SUMMARY OF THE INVENTION

The present invention is directed to the compound of the formula (I):

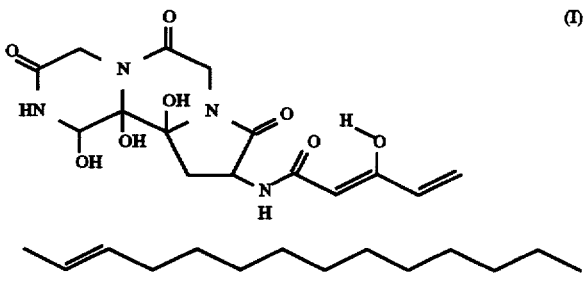

The compound has antimicrobial and fungicidal properties and may be useful for controlling systemic and superficial fungal infections in humans with fewer side effects than standard antifungal agents such as amphotericin B or fluconazole. Additionally, the compound exhibits activity against plant fungal pathogens and may be useful as a broad spectrum crop antifungal agent.

The compound is obtained by cultivation of a strain of the fungus, *Sporormiella minimoides*, MF 5867, in the culture collection of Merck & Co., Inc., Rahway, N.J.

DETAILED DESCRIPTION OF THE INVENTION

The compound obtained is an off-white solid and is characterized by the following spectral properties:

ULTRAVIOLET SPECTRAL DATA

The ultraviolet spectrum of Compound I was recorded on a Beckman DU-70 spectrophotometer.

$\lambda_{max}$(MeOH):283 nm($\epsilon$=9900)

OPTICAL ROTATION DATA

The optical rotation of Compound I was recorded on a Perkin Elmer 241 polarimeter at 20° C. in MeOH.

$[\alpha]_D^{20}$=+10°(c 0.65)

INFRARED SPECTRAL DATA

The infrared data for Compound I was recorded on the Perkin Elmer Model 1750 FT infrared spectrometer as a thin film on ZnSe. 3301, 2924,2854, 1680, 1590, 1547, 1412, 1204,1080, 998 cm$^{-1}$

MASS SPECTRAL DATA

Mass spectra were recorded on JEOL SX-102A (Electron Impact, EI, 90eV) and JEOL HX110 (Fast Atom Bombardment, FAB) mass spectrometers. The FAB spectrum was run in a matrix of dithiothreitol-dithioerythritol (20/80). The exact mass measurements were made at high resolution with Ultramark™ 1960 (Fomblin) as the reference compound.

The molecular weight was determined by EI-MS as the hexa-TMS derivative (observed at m/z 994) and by FAB-MS (observed as M+H at m/z 563).

| HR-FABMS | Found for $C_{28}H_{42}N_4O_8$ + H | 563.3110 |
|---|---|---|
| | Calculated | 563.3081 |

NMR SPECTRAL DATA

NMR spectra were recorded in CD$_3$OD at 500 MHz ($^1$H) or 125 MHz ($^{13}$C). Chemical shifts are reported downfield from TMS (tetramethylsilane) and spectra were referenced to the solvent peaks (3.30 ppm for $^1$H spectra and 49.0 ppm for $^{13}$C spectra).

$^1$H NMR SPECTRA

H NMR in d$_8$-THF: δ0.89 (t, 7, 3H), 1.29 (m, 16H), 1.42 (m, 2H), 2.14 (m, 2H), 2.43 (dd, 8.5, 13, 1H), 2.58 (dd, 9, 13, 1H), 3.77 (d, 18, 1H), 3.79 (d, 18, 1H), 4.166 (d, 18, 1H), 4.170 (d, 18, 1H), 4.82 (q, 8.5, 1H), 4.96 (d, 5.5, 1H), 5.05 (s, 1H), 5.83 (d, 15.5, 1H), 5.98 (m, 1H), 6.16 (dd, 11, 15, 1H), 6.31 (brs, -OH, 1H), 6.40 (brs, -OH, 1H), 6.76 (brs, -OH, 1H), 6.93 (dd, 11, 15, 1H), 7.83 (d, 8, -NH, 1H), 8.52 (d, 5.5, -NH, 1H), 13.66 (d, 1.5, -OH, 1H).

$^{13}$C NMR SPECTRA $^{13}$C NMR in d$_8$-THF: δ14.8, 23.9, 30.27, 30.46, 30.67, 30.79, 30.91, 30.93, 30.95, 33.2, 34.1, 38.1, 43.2, 45.5, 50.0, 78.2, 81.7, 88.1, 93.5, 125.5, 130.7, 136.3, 141.1, 165.5, 168.2, 168.5, 171.3, 173.5.

The compound of this invention has antimicrobial properties and is especially useful as an antifungal agent against both filamentous fungi and yeasts. It is useful against organisms causing systemic human pathogenic mycotic infections such as *Candida albicans*, *Candida tropicalis*, *Candida guillermondii*, *Candida glabrata*, *Aspergillus fumigatus*, *Candida pseudotropicalis*, *Saccharomyces cerevisiae*, *Aspergillus flavus* et al. It is also useful against organisms causing superficial fungal infections such as *Trichoderma sp.* and *Candida sp.* These properties may be effectively utilized by administering compositions containing an antifungal amount of the compound to an area, object or subject, on or in which fungi are to be controlled. Thus, compositions containing an antifungally effective amount of the compound and their use for the control of fungi are aspects of the present invention. An especially preferred aspect of the present invention are compositions in a pharmaceutically acceptable carrier and their use for the control of mycotic infections by administering a therapeutically effective amount of the compound.

The compound of this invention also has agricultural antifungal properties. Compound I is useful as an antifungal agent against certain Oomycetes on plants, including potato late blight, *Phytophthora infestans*. It is also useful as an antifungal agent for control of conidial Ascomycetes (e.g., grey mold, *Botrytis cinerea*, early blight, *Alternaria solani*, and glume blotch, *Septoria nodorum*). These properties may be utilized by administering compositions containing an antifungal amount of the compound to an area, object or subject, on or in which fungi are to be controlled. When the term control is used, it is intended to imply both prophylactic use and curative use of the compound.

Depending on the circumstances (such as the type of crop where fungi are to be combatted, the environmental conditions, or other factors), the composition of the present invention in addition to the antifungal compound may also contain other active ingredients such as biocides, pesticides, herbicides, insecticides, nematocides, acaricides or plant nutrients or fertilizers.

The compound is not limited to utility as a medicament; it may be used in other ways. For example, it may be used as an additive to animal feed, as a preservative or antifungal sterilizing agent for food preparation, as a disinfectant and in other industrial systems where control of fungal growth is desired. It may be employed in concentrations ranging from about 0.01 to about 100 parts per million to destroy or inhibit the growth of fungal organisms in water based paints and to inhibit the growth of harmful bacteria in the white water of paper mills.

The compound of the present invention is a natural product produced from a strain of *Sporormiella minimoides* Ahmed & Cain (Ascomycotina, Pleosporales), MF 5867, in the culture collection of Merck & Co., Inc., Rahway, N.J. The fungi has been deposited under the Budapest Treaty in the culture collection of the American Type Culture Collection on Jun. 20, 1996 at 12301 Parklawn Drive, Rockville, Md. 20852 and assigned accession number ATCC 74372.

The producing organism was isolated from giraffe dung collected in Namutoni, Namibia.

In the following description, all capitalized color names are from Ridgway, 1912. In agar cultures, colonies of the fungus exhibit the following morphology:

On oatmeal agar (Difco), colony attaining a diameter of 55 mm after 17 days at 25 C. and 67% relative humidity in 12 hr photoperiod in fluorescent light. Colony mat appressed, deeply sulcate, the surface with a roughened appearance due to ascomata formation, olivaceous gray (Iron Gray, Dark Olive Gray); margin white, entire; reverse, soluble pigment and exudate absent.

On potato-dextrose agar (Difco), colony attaining a diameter of 64 mm after 17 days under the same incubation conditions. Colony mat appressed to velvety, deeply sulcate, dark olivaceous (Dark Olive Gray), slightly iridescent; margin hyaline, entire; reverse, soluble pigment and exudate absent.

On cornmeal agar (Difco), colony attaining a diameter of 48 mm after 17 days under the same incubation conditions. Colony mat hyaline appressed; margin hyaline, uneven; brown to black perithecia scattered throughout mat, most abundant near inoculation point; reverse, soluble pigment and exudate absent.

On MYE (1% malt extract, 0.2 % yeast extract (both Difco)), colony attaining a diameter of 60 mm after 17 days under the same incubation conditions. Colony mat appressed, greenish gray to gray (Grayish Olive, Light Grayish Olive); margin hyaline, entire; reverse soluble pigment and exudate absent; rare perithecia present near the inoculation point.

On MYE (1% malt extract, 0.2 % yeast extract (both Difco)), at 37° C. and in the dark, attaining a diameter of 31 mm after 17 days growth, culture mat appressed to velvety, light yellow (Naples Yellow, Straw Yellow); margin hyaline, uneven, growing into agar surface; reverse, soluble pigment and exudate absent.

Ascomata are perithecia, mostly subglobose to pyriform, scattered, immersed, olivaceous to dark brown, 200–240× 130–150 μm, smooth, neck papilliform. Asci subcylindrical, rounded at top, abruptly constricted at base to form a short stipe, 8-spored, hyaline, 90–100×15–20 μm. Ascospores cylindrical, biseriately arranged at an oblique angle, olivaceous to dark brown, 4-celled, cells easily separable, transversely septate, germ slit at an oblique angle, gelatinous sheath narrow.

Although the invention is discussed principally with respect to the specific strain, it is well known in the art that the properties of microorganisms can be varied naturally and artificially. Thus, all strains derived from *Sporormiella minimoides* MF 5867, ATCC 74372 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

The production of the compound may be carried out by cultivating *Sporormiella minimoides* MF 5867, ATCC 74372 in a suitable nutrient medium under conditions described herein until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate the compound from other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium. These, however, are merely illustrative of the wide variety of media which may be employed and are not intended to be limiting.

TABLE 1

| KF SEED MEDIUM | | Trace Element Mix | |
|---|---|---|---|
| | per liter | | per liter |
| Corn Steep Liquor | 5 g | $FeSO_4.7H_2O$ | 1 g |
| Tomato Paste | 40 g | $MnSO_4.4H_2O$ | 1 g |
| Oat flour | 10 g | $CuCl_2.2H_2O$ | 25 mg |
| Glucose | 10 g | $CaCl_2$ | 100 mg |
| Trace Element Mix | 10 ml | $H_3BO_3$ | 56 mg |
| | | $(NH_4)_6Mo_7O_{24}.4H_2O$ | 19 mg |
| pH = 6.8 | | $ZnSO_4.7H_2O$ | 200 mg |

TABLE 2

Table 2. Production Medium CYS80

| Component | per liter |
|---|---|
| Sucrose | 80 g |
| Yellow Corn Meal | 50 g |
| Fidco Yeast Extract | 1 g | pH adjusted to 6.1 with NaOH before autoclaving.

TABLE 3

Production Medium CYS80-7

| Component | per liter |
|---|---|
| Fructose | 80 g |
| Yellow Corn Meal | 50 g |
| Fidco Yeast Extract | 6 g |
| MES* | 16.2 g | pH adjusted to 6.1 with NaOH before autoclaving.
*[2-(N-morpholino)-ethanesulfonic acid], monohydrate (MES)

TABLE 4

Production Medium CYS80-8

| Component | per liter |
|---|---|
| Fructose | 80 g |
| Yellow Corn Meal | 50 g |
| Fidco Yeast Extract | 8 g |
| Phenylalanine | 10 g |
| $ZnSO_4.7H_2O$ | 100 mg |
| MES* | 16.2 g | pH adjusted to 6.1 with NaOH before autoclaving.
*[2-(N-morpholino)-ethanesulfonic acid], monohydrate (MES)

The CYS80-8 production medium was found to give the best yield of the compound. In the production of the compound, generally, the culture is first grown in a seed medium and the culture growth then used to inoculate a production medium. The production medium may be a solid medium or a liquid medium.

FERMENTATION

Fermentation conditions for the production of Compound I by *Sporormiella minimoides* were as follows: Vegetative mycelia of the culture were prepared by inoculating 54 mL of KF seed medium (Table 1) in a 250-ml unbaffled Erlenmeyer flask with 2 ml of mycelia in 10% glycerol (MF5867) that had been stored at −80° C. Seed cultures were incubated for 3 days at 25° C. and 85% relative humidity on a rotary shaker with a 5-cm throw at 220 rpm in a room with constant fluorescent light. Two-ml portions of the culture were then used to inoculate a second stage seed culture and further incubated for 3 days as stated above. Two-ml portions of this 3 day culture were used to inoculate 50-ml portions of liquid production media CYS80, CYS80-7 or CYS80-8 (Table 2, 3 and 4 respectively) in 250 ml unbaffled Erlenmeyer flasks. All incubation parameters remained the same as stated above for seed medium. Maximal production of Compound I in medium CYS80-7 occurred at day 18 (13 mg/L). In medium CYS80-8 maximal production of Compound I occurred at day 18 (19 mg/L). At harvest, Compound I was extracted from the cell pellet with equal volume of methanol by shaking with the solvent at 220 rpm for 1 hour at 25° C. The samples were centrifuged for 20 minutes at 3000 rpm to obtain clear extract. Both the methanol and aqueous layers were analyzed by HPLC.

The usefulness of the compound as an antifungal agent, especially as an antimycotic agent, may be demonstrated with the compound in a broth microdilution assay for the determination of minimum inhibitory concentration (MIC) and minimum fungicidal concentration (MFC) against fungi. The compound is found to be effective in the assay against a panel of fungi selected for their resistance/susceptibility to known compounds, animal virulence, source and clinical importance, at concentrations comparable to an established antifungal agent, amphotericin B.

In the microbroth dilution assay, microorganisms were selected by streaking a yeast culture on Sabouraud dextrose agar (SDA) and incubating for 24–48 hours at 35°–37° C. Three to five characteristic colonies were selected and transferred to a fresh plate and incubated under similar conditions. From the regrowth, 3 to 5 colonies were selected and suspended in 10 milliliters of YM broth (Difco) and incubated for 4 hours at 35°–37° C. shaking at 225 rpm. The 4 hour broth cultures were adjusted optically to 86% transmission resulting in a concentration of $1-5 \times 10^6$ cfu/ml which was further diluted 1:100 in YNBD (yeast nitrogen base with 2% dextrose) to obtain a concentration of $1-\times 10^4$ cfu/ml for use as inocula.

The test compound was dissolved at 128 µg/ml in 20% methanol and diluted 2×into the first well to achieve a concentration of 64 µg/ml at 10% methanol in the first well (column 1) of a 96-well, U-bottomed plate. The compound was subsequently serially diluted 2×by transferring 75 µl of said solution from well to well across the plate into 75 µl of YNBD media. The plates containing the diluted compounds were then inoculated with 75 µl/well of the appropriate microorganism resulting in an additional 2×dilution of compound to yield concentrations from 32 µg/ml to 0.0078 µg/ml.

Amphotericin B, the control compound, was prepared as a stock solution of 256 µg/ml in 10% DMSO and 150 µl of said solution delivered to column 1 of a 96-well, U-bottomed plate. The compounds in column 1 were then serially diluted two-fold and inoculated with the appropriate microorganism to yield concentrations from 128 µg/ml to 0.03 µg/ml.

The plates were incubated for 48 hours at 35–37° C. with MIC (minimum inhibitory concentration) determinations carried out after 24 hours of incubation (except Cryptococcus strains which are read at 48 hours). Growth and sterility controls for each organism and sterility checks for the compounds also were carried out.

After recording MICs at 24 hours, the microtiter plates were shaken gently to resuspend the cells. A 1.5 µl sample was transferred from each well of the 96-well plate to a single reservoir inoculum plate containing SDA. The inoculated SDA and corresponding microtiter plates were incubated for 24 hours at 35–37° C. For *Cryptococcus neoformans*, SDA plates were inoculated at 48 hours after recording MICs and incubated 48 hours before reading the MFC. MFC is the lowest concentration of compound at which either no growth or growth of <4 colonies occur.

Minimum Fungicidal Concentration (MFC)
Minimum Inhibitory Concentration (MIC)
μg/ml

| Strain | MIC | MFC |
|---|---|---|
| Candida albicans (MY1028) | 0.125 | 0.25 |
| Candida albicans (MY1055) | 0.125 | 0.125 |
| Candida albicans (MY1750) | 0.25 | 0.25 |
| Candida guillermondii (MY1019) | 2 | 2 |
| Candida parapsilosis (MY1010) | 0.125 | 0.125 |
| Candida pseudotropicalis (MY2099) | 0.25 | 0.5 |
| Candida tropicalis (MY1012) | 0.125 | 0.125 |
| Cryptococcus neoformans (MY1051) | 0.125 | 0.5 |
| Cryptococcus neoformans (MY1146) | 4 | 8 |
| Cryptococcus neoformans (MY2061) | 0.25 | 2 |
| Cryptococcus neoformans (MY2062) | 16 | >32 |
| Saccharomyces cerevisiae (MY1976) | 0.25 | 0.125 |
| Aspergillus fumigatus (MF4839) | 1 | |
| Aspergillus fumigatus (5668) | 2 | |
| Aspergillus fumigatus (5669) | 2 | |

The compound is also useful for inhibiting the growth of filamentous fungi. Such use may be illustrated in the following tests with *Aspergillus flavus*, *Fusarium oxysporum*, *Ustilago zeae* and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied directly to the agar plates as methanol solutions. When the sample to be tested is crude broth, it may be centrifuged prior to application. The assay plates are then incubated at either 28° C. or 37° C. for 24 hours. Following incubation, the inhibition zones are measured. Effects on growth are also noted as to appearance. The compound is seen to effectively inhibit growth of the fungal organisms.

Compound I is also useful as a broad spectrum antifungal agent for agricultural use as shown in an in vitro assay using various phytopathogens. In such an assay against a panel of four phytopathogens with significant agricultural importance: late blight, *Phytophthora infestans*; early blight, *Alternaria solani*; glume blotch, *Septoria nodorum*; and grey mold, *Botrytis cinerea*; Compound I is found to be active.

In the in vitro assay, the phytopathogens were maintained on V8 agar for two weeks at 19–21° C. At this stage, to harvest fungal spores for inoculum, the plates were flooded with % clarified V8 broth and the mycelia surface gently scraped with a rubber policeman. The broth/spore mixture was then filtered through three layers of cheesecloth and the concentration of spored determine by hemocytometer. The spore suspension was then diluted to yield a final concentration of $5 \times 10^3$ for *A. solani*; $1 \times 10^4$ for *B. cinerea*; $2 \times 10^4$ for *P. infestans*; and $5 \times 10^4$ for *S. nodorum*: for use as inoculum.

The test compound, Compound I, and control compounds were prepared as stock solutions of 2mg/ml in 10% DMSO. Into row 1 of a 96-well microtiter plate, 20 μl of said stock solutions were added. The compounds in row 1 were then serially diluted with 10% DMSO and ultimately diluted with 90μl of inoculum (Total Volume 100 μl) of the appropriate phytopathogen. This yielded concentration ranging from 20 μg/ml to 0.156 μg/ml. The microtiter plates were then incubated at 19°–21° C. for either two days (for *B. cinerea*, *A. solani*, *S. nodorum*) or four days (*P. infestans*) after which MIC (minimum inhibitory concentration) values were determined for each species.

Growth of all four phytopathogens tested was inhibited by Compound I, with MIC's of 10 μg/ml for *P. infestans*; 20 μg/ml for *B. cinerea*; 10 μg/ml for *S. nodorum*; and 20 μg/ml for *A.solani*.

In view of the broad spectrum of activity, the product of the present invention either singly or as a mixture is adaptable to being utilized in various applications of antifungal compositions. In such case, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compound may be combined with a pharmaceutically acceptable carrier, the nature of which will depend on whether the composition is to be topical, parenteral or oral.

The compound of the invention may be used in a variety of pharmaceutical preparations. Compositions for injection may be prepared in unit dosage form in ampoules or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the compound may be in the form of a sterile powder, which can be reconstituted with a suitable carrier such as sterile water, normal saline and the like at the time of administration. The powder can be in lyophilized or non-lyophilized form.

Oral compositions are typically in the form of tablets, capsules, solutions or suspensions. Such compositions may likewise be packaged in unit dose or multidose containers. In these oral compositions, the pharmaceutically acceptable carriers may be comprised of diluents, tabletting and granulating aids, lubricants, disintegrants, buffers, flavorants, sweeteners, preservatives and the like.

Compositions for oral administration may be prepared by mixing the component drugs with any of the usual pharmaceutical media, including for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricants such as calcium stearate, together with binders, disintegrating agents and the like.

For topical applications, the drug may be formulated in conventional creams and ointments such as white petrolatum, anhydrous lanolin, cetyl alcohol, cold cream, glyceryl monostearate, rose water and the like. The preferred compositions for superficial fungal infections are topical creams, ointments, solutions and sprays.

For parenteral applications, the compounds may be formulated in conventional parenteral solutions such as 0.85 percent sodium chloride or 5% dextrose in water, or other pharmaceutically acceptable compositions.

The preferred method of parenteral administration of the compound of formula I is by intravenous (i.v.) infusion. Alternatively, the compound may be administered intramuscularly (i.m.).

The invention described herein further includes a method of treating a fungal infection in a mammal in need of such treatment, comprising administering to said mammal a compound in accordance with formula I in an amount effective to treat a fungal infection.

The dosage to be administered depends to a large extent upon the condition and size of the subject being treated as well as the route and frequency of administration. The parenteral route (by injection) is preferred for generalized infections. Such matters, however, are typically left to the discretion of the clinician according to principles of treatment well known in the infectious disease arts.

The compositions for human delivery per unit dosage, whether liquid or solid, may contain from about 0.01% to about 99% of active material, the preferred range being from about 1.0–60%. The composition will generally contain from about 1.5 mg to about 2000 mg of the active ingredient; however, in general, it is preferable to employ a dosage amount in the range of from about 25 mg to 1000 mg. In parenteral administration, the unit dosage is usually the compound I in a sterile water or saline solution or in the form of a soluble powder intended for solution.

For adults, a dose of about 0.5 to about 50 mg of the formula I compound per kg of body weight is administered from 1 to 6 times per day. The preferred dosage ranges from about 2 mg to 1000 mg of the compound may given one to four times per day.

More specifically, for mild infections a dose of about 2.5–250 mg two to four times daily is preferred. For moderate infections against highly susceptible organisms a dose of about 5–500 mg b.i.d. to q.i.d. is preferred. For severe, life-threatening infections against organisms at the upper limits of sensitivity, a dose of about 10–2000 mg two to six times daily is preferred.

For children, a dose of 0.5–25 mg/kg of body weight given 1 to 4 times per day is preferred; a dose of 1.0- mg/kg b.i.d., t.i.d. or q.i.d. is preferred.

For non-medical application, the product of the present invention, either alone or as a mixture, may be employed in compositions in an inert carrier which included finely divided dry or liquid diluents, extenders, fillers, conditioners and excipients, including various clays, diatomaceous earth, talc, and the like or water and various organic liquids such as lower alkanols, such as ethanol and isopropanol, or kerosene, benzene, toluene and other petroleum distillate fractions or mixtures thereof.

The following example illustrates the invention but is not to be construed as limiting the invention disclosed herein.

EXAMPLE I

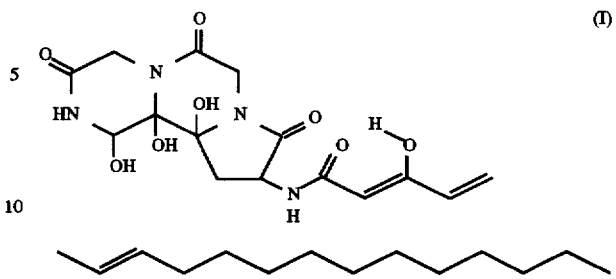

ISOLATION OF COMPOUND I

The MeOH extract of 2.4 L of whole broth fermentation of culture (MF5867) was filtered through a celite pad. The filtrate was adjusted to 75% aqueous with 0.01 M ammonium citrate buffer at pH 4.7. A 3.3 L portion was applied to a 100 mL Diaion SP 207 column equilibrated with 25% MeOH and 75% 0.01 M ammonium citrate buffer. The column was rinsed with 400 mL of 25% MeOH and 75% citrate buffer followed by elution with 400 mL each of 50%, 75% and 100% MeOH in aqueous 0.01 M ammonium citrate adjusted to pH 4.7. Twenty 20 mL fractions were collected for each eluent solution. The product rich fractions 6–20 (100% MeOH) were combined.

The crude fraction pool was concentrated in vacuo to a syrup with a total dry weight of 234 mg. This material was dissolved in a minimum of 60% hexanes, 20% MeOH and 20% toluene. The solution was applied to an 85 mL Sephadex LH-20 column that was equilibrated with the hexanes-:MeOH:toluene solution. The column was eluted with 350 mL of the same hexanes solution and seventy 5 mL fractions were collected. The product rich fractions 29–38 were combined.

A 3.8 mg portion of the LH-20 rich cut was further purified by HPLC separation (Zorbax Rx-C8, 5 µm, 9.4 mm×250 mm, eluted with mobile phase consisting of 65% methanol/35% aqueous 0.01 M citrate adjusted to pH 4.7 with concentrated $NH_4OH$, flow rate 3.5 mL/min. at 55° C., diode array detection). Sixty 3.5 mL fractions were collected. The product rich fractions 33–45 were determined by biological assay. These active fractions associated with a poorly shaped double peak indicating a UV maximum at 280 nm.

The fractions were pooled and diluted from approximately 65% MeOH to 50% MeOH with $H_2O$. The solution was desalted on a 2 mL SP 207 column that had been equilibrated with a comparable solution of HPLC mobile phase and $H_2O$. The column was eluted with 25 mL of MeOH in one 1 mL aliquot followed by twelve 2 mL fractions. The rich cut containing Compound I was contained in fractions 3–8 which were combined.

ISOLATION OF COMPOUND I

Thirty-five liters whole broth fermentation of culture (MF5867) was processed through a continuous feed centrifuge (CEPA High Speed Separator) separating the supernant from the solids. The solids were saturated with approximately 21 L of MeOH and stirred for over three hours. The MeOH extract was filtered through a celite pad and the solids were rinsed with an additional 4 L of MeOH. The filtrate was retained and the remaining solids were re-extracted with approximately 27 L of MeOH. This solution was also filtered through a celite pad. Both filtrates were adjusted to 50% aqueous with 0.01 M ammonium citrate buffer at pH 4.7. The combined 84.5 L of diluted filtrate was applied to a two liter Diaion SP 207 column equilibrated with 50% MeOH and 50% 0.01 M ammonium citrate buffer. The column was rinsed with 8 L of 75% MeOH and 25% citrate buffer followed by elution with 11 L of MeOH. One 1 L and five 2 L MeOH fractions were collected. The product rich fractions 2–6 were determined by RP HPLC assay (Zorbax Rx-C8, 5 µm, 4.6 mm×250 mm, eluted with mobile phase consisting of 65% methanol/35% aqueous 0.01 M citrate adjusted to pH 4.7 with concentrated $NH_4OH$, flow rate 1.0 mL/min. at 55° C., diode array detection).

The crude fraction pool was concentrated in vacuo to approximately 800 mL with a total dry weight of 15.6 g. A 4.9 g portion was dissolved in 100 mL of 60% hexanes, 20% MeOH and 20% toluene. This solution was applied to a two liter Sephadex LH-20 column that was equilibrated with the hexanes:MeOH:toluene solution. The column was eluted with 4.5 L of the same hexanes solution and thirty-six 250 mL fractions were collected. The product rich fractions 15–21 (673 mg) were determined by RP HPLC assay (Phenomenex Primesphere C8, 5 µm, 4.6 mm×250 mm, eluted with mobile phase consisting of 80% methanol/20% aqueous 0.025 M acetate adjusted to pH 4.7 with concentrated $NH_4OH$, flow rate 1.0 mL/min. at 40° C., diode array detection).

This sample was further purified in two identical HPLC separations (Phenomenex Primesphere C8, 15 mm, 5.0 cm×25.0 cm, eluted with mobile phase consisting of 80% methanol/20% aqueous 0.025 M acetate adjusted to pH 4.7 with concentrated $NH_4OH$, flow rate 60 mL/min. at room temperature, detection at 280 nm). The crude pool was dissolved in 4.4 mL of THF and diluted with 2.0 mL of the acetate buffer. This solution was divided into two injections. Twenty-four milliliter fractions were collected. The product rich fractions 83–97 and 78–100 from the first and second separations, respectively, were pooled together and concentrated in vacuo to approximately thirty percent of the original volume. The solution was diluted to 400 mL with $H_2O$, acidified, and extracted twice with an equal volume of ethyl acetate. The combined ethyl acetate layers were washed with an equal volume of brine, dried over anhydrous $Na_2SO_4$ and concentrated in vacuo to yield 64.6 milligrams of Compound I.

Compound I has the spectral properties previously described.

The following examples illustrate representative compositions containing Compound I.

EXAMPLE A 1000 compressed tablets each containing 500 milligrams of Compound I are prepared from the following formulation:

| | |
|---|---|
| Compound I | 500 g |
| Starch | 750 g |
| Dibasic calcium phosphate hydrous | 5000 g |
| Calcium stearate | 2.5 g |

The finely powdered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

| | |
|---|---|
| Compound | 500 g |
| Starch | 250 g |
| Lactose | 750 g |
| Talc | 250 g |
| Calcium stearate | 10 g |

A uniform mixture of the ingredients is prepared by blending and used to fill two-piece hard gelatin capsules.

EXAMPLE C 250 milliliters of an injectible solution are prepared by conventional procedures from the following formulation:

| | |
|---|---|
| Dextrose | 12.5 g |
| Water | 250 ml |
| Compound I | 400 mg |

The ingredients are blended and sterilized for use.

EXAMPLE D

An ointment suitable for topical application may be prepared by intimately dispersing 13 mg of Compound I in 1 g of commercially available polyethylene/hydrocarbon gel.

EXAMPLE E

An aerosol composition may be prepared having the following formulation (per canister):

| | |
|---|---|
| Compound I | 24 mg |
| Lecithin NF, liquid concentrate | 1.2 mg |
| Trichlorofluoromethane | 4.025 g |
| Dichlorodifluoromethane | 12.15 g |

The preferred embodiments of the invention have been described herein in detail. However, numerous alternative embodiments are contemplated as falling within the scope of the invention. Therefore, the scope of the claims is not to be limited to the specific teachings contained herein.

What is claimed is:

1. A compound having the structure:

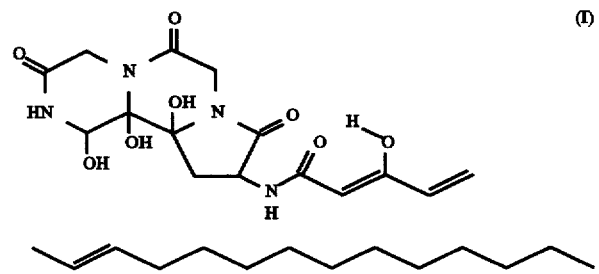

2. An antifungal composition which comprises an effective amount of the compound of claim 1 in combination with a biologically inert carrier or diluent.

3. A pharmaceutical composition which comprises an effective amount of the compound of claim 1 in combination with a pharmaceutically acceptable carrier.

4. An antifungal composition which comprises an effective amount of the compound of claim 1 in combination with an agrochemically compatible carrier or diluent.

5. A method for controlling fungal growth which comprises administering to the site where growth is to be controlled, an effective amount of the compound of claim 1.

6. A method for treating a fungal infection in a subject which comprises administering to a region of the subject afflicted with said fungal infection a therapeutically effective amount of the compound of claim 1.

7. A method of combatting fungi in plants which comprises administering to a plant region afflicted with said fungi an effective amount of the compound of claim 1.

8. A method for treating agricultural fungal infections which comprises administering to the site where growth is to be treated an effective amount of the compound of claim 1.

* * * * *

UNITED STATES PATENT AND TRADEMARK OFFICE
CERTIFICATE OF CORRECTION

PATENT NO. : 5,801,172
DATED : September 1, 1998
INVENTOR(S) : Clapp-Shapiro, et. al.

It is certified that error appears in the above-identified patent and that said Letters Patent is hereby corrected as shown below:

Title page, item [54], and col. 1, lines 1-2, should read --
ANTIFUNGAL AGENT FROM SPORORMIELLA MINIMOIDES Signed and Sealed this Fifteenth Day of December, 1998

*Attest:*

BRUCE LEHMAN

*Attesting Officer*     *Commissioner of Patents and Trademarks*